United States Patent
Nielsen et al.

(10) Patent No.: US 10,413,747 B2
(45) Date of Patent: Sep. 17, 2019

(54) IMPLANTABLE DEVICE WITH OPTICAL LEAD CONNECTOR

(71) Applicant: Medtronic, Inc., Minneapolis, MN (US)

(72) Inventors: Christian S. Nielsen, River Falls, WI (US); Kunal J. Paralikar, Minneapolis, MN (US); Brad C. Tischendorf, Minneapolis, MN (US); John D. Norton, St. Paul, MN (US); Markus W. Reiterer, Plymouth, MN (US); Andrew J. Thom, Maple Grove, MN (US); Gordon O. Munns, Stacy, MN (US)

(73) Assignee: Medtronic, Inc., Minneapolis, MN (US)

(*) Notice: Subject to any disclaimer, the term of this patent is extended or adjusted under 35 U.S.C. 154(b) by 373 days.

(21) Appl. No.: 14/694,095

(22) Filed: Apr. 23, 2015

(65) Prior Publication Data

US 2015/0306414 A1    Oct. 29, 2015

Related U.S. Application Data

(60) Provisional application No. 61/984,332, filed on Apr. 25, 2014.

(51) Int. Cl.
*A61N 1/375*  (2006.01)
*A61N 1/05*  (2006.01)
(Continued)

(52) U.S. Cl.
CPC ............ *A61N 5/0601* (2013.01); *A61N 1/05* (2013.01); *A61N 1/3752* (2013.01); *A61N 5/0622* (2013.01); *G02B 6/0008* (2013.01); *G02B 6/4248* (2013.01); *A61N 2005/063* (2013.01); *A61N 2005/0659* (2013.01); *A61N 2005/0661* (2013.01); *A61N 2005/0662* (2013.01)

(58) Field of Classification Search
CPC .. A61N 2005/063; A61N 1/3752; A61N 1/05; A61N 1/375
See application file for complete search history.

(56) References Cited

U.S. PATENT DOCUMENTS 5,445,608 A    8/1995  Chen et al.
5,556,421 A *  9/1996  Prutchi ................ A61B 5/1459
                                                     607/36
(Continued)

FOREIGN PATENT DOCUMENTS

WO    WO 2008/105691 A1    9/2008

OTHER PUBLICATIONS

PCT Patent Application No. PCT/US2015/027228, filed Apr. 23, 2015; International Search Report / Written Opinion; dated Jul. 24, 2015; 11 pages.
(Continued)

*Primary Examiner* — William J Levicky
(74) *Attorney, Agent, or Firm* — Mueting, Raasch & Gebhardt, P.A.

(57) ABSTRACT

An implantable active medical device includes a housing defining a hermetic cavity, a lead connector receptacle extending into the implantable active medical device, and a solid state light source disposed within the hermetic cavity and optically coupled to the lead connector receptacle.

14 Claims, 4 Drawing Sheets

(51) Int. Cl.
*A61N 5/06* (2006.01)
*G02B 6/42* (2006.01)
*F21V 8/00* (2006.01)

(56) References Cited

U.S. PATENT DOCUMENTS

| | | | |
|---|---|---|---|
| 5,902,236 A | 5/1999 | Iversen | |
| 6,198,952 B1* | 3/2001 | Miesel | A61B 5/1459 |
| | | | 600/333 |
| 7,349,618 B2 | 3/2008 | Nielsen et al. | |
| 7,519,261 B2 | 4/2009 | Nielsen et al. | |
| 8,192,418 B2 | 6/2012 | Robinson et al. | |
| 8,288,654 B2 | 10/2012 | Taylor et al. | |
| 8,396,570 B2* | 3/2013 | Dadd | A61N 1/36036 |
| | | | 607/137 |
| 8,538,530 B1* | 9/2013 | Orinski | A61N 1/3754 |
| | | | 607/36 |
| 8,936,630 B2* | 1/2015 | Denison | A61N 5/0601 |
| | | | 607/88 |
| 2002/0082651 A1 | 6/2002 | Stahmann | A61N 1/3622 |
| | | | 607/9 |
| 2005/0070987 A1* | 3/2005 | Erickson | A61N 1/05 |
| | | | 607/122 |
| 2008/0077190 A1* | 3/2008 | Kane | A61N 1/3752 |
| | | | 607/37 |
| 2008/0177167 A1* | 7/2008 | Janzig | A61N 1/3752 |
| | | | 600/373 |
| 2010/0174329 A1 | 7/2010 | Dadd et al. | |
| 2010/0230392 A1 | 9/2010 | Robinson et al. | |
| 2011/0125077 A1 | 5/2011 | Denison et al. | |
| 2011/0125078 A1 | 5/2011 | Denison et al. | |
| 2013/0030353 A1 | 1/2013 | Seymour et al. | |
| 2013/0035733 A1 | 2/2013 | Breyen et al. | |
| 2014/0330341 A1* | 11/2014 | Wolf, II | A61N 1/36071 |
| | | | 607/46 |

OTHER PUBLICATIONS

U.S. Appl. No. 60/865,763, filed Nov. 14, 2006, Thom et al.
PCT Patent Application No. PCT/US2015/027231, filed Apr. 23, 2015; Invitation to Pay Additional Fees; dated Aug. 4, 2015; 5 pages.
PCT Patent Application No. PCT/US2015/027231, filed Apr. 23, 2015; International Search Report / Written Opinion; dated Oct. 16, 2015; 13 pages.
Campagnola, et at., "Fiber-coupled light-emitting diode for localized photostimulation of neurons expressing channelrhodopsin-2", 2008, *Journal of Neuroscience Methods*, 169:27-33.

* cited by examiner

IMPLANTABLE DEVICE WITH OPTICAL LEAD CONNECTOR

CROSS REFERENCE

This application claims the benefit of U.S. Provisional Application Ser. No. 61/984,332, filed Apr. 25, 2014, which is incorporated by reference herein.

BACKGROUND

An implantable active medical devices (IMDs), also known as "active implantable medical device" (AIMD) can be equipped with bioactuator systems capable of providing light therapy or biosensor systems capable of monitoring optical characteristics (e.g., changes in refractive index or reflectivity) indicative of physiological conditions (e.g., temperature, pressure, blood oxygen content, rate of chemical processing, etc.). An IMD may be equipped with, for example, a fiber-linked optical interferometric system capable of monitoring hydrostatic pressure at a chosen site within a patient's body; e.g., blood pressure within an artery. In such a system, the proximal end of a flexible, elongated catheter is coupled to an IMD and the distal end of the catheter is positioned adjacent the site to be optically monitored. The catheter carries an optical fiber, which is optically coupled to a transceiver disposed within the IMD's canister. The transceiver directs outgoing light signals into the proximal end of the fiber, which propagate through the optical fiber until they reach the fiber's distal end. The light signals are then modulated by the body fluid (e.g., blood) being monitored and are reflected back into the fiber. The modulated signals propagate through the optical fiber once again and are received by the transceiver at the fiber's proximal end. The transceiver analyzes characteristics (e.g., amplitude in an interferometer) of the returning signals, and control circuitry coupled to the transceiver determines the blood pressure at the distal end of the catheter.

An optical feedthrough is utilized to guide the optical fiber through the canister of the IMD. The feedthrough may include a ferrule (e.g., titanium) having an aperture there, through which the optical fiber passes. To protect the circuitry of the IMD and to secure the optical fiber within the ferrule, a hermetic seal is formed between an inner surface of the ferrule and an outer surface of the optic fiber. Traditionally, the hermetic seal has been formed by way of a co-firing or brazing process. For example, a window-ferrule braze may be formed by threading an annular ceramic or metal (e.g., gold) preform over the window and positioning the preform against an inner shelf provided within the ferrule. If a matched seal is to be formed, the components are chosen to have similar coefficients of thermal expansion, and an inner surface of the ferrule may be metalized prior to insertion of the preform. Next, the feedthrough assembly is heated in a furnace (e.g., to over 700 degrees Celsius for approximately 10-15 minutes) to cause the brazing compound to wet the glass and flow against the ferrule to form a seal. An annealing step is then performed, and the feedthrough assembly is allowed to cool to room temperature.

BRIEF SUMMARY

The present disclosure relates to an implantable medical device with an optical lead connector. In particular the present disclosure relates to an implantable medical device having a lead connector receptacle that optically couples to a lead. An optical feedthrough forms a portion of the lead connector receptacle and a solid state light source is disposed within the implantable medical device hermetic housing.

In one illustrative embodiment, an implantable active medical device includes a housing defining a hermetic cavity, a lead connector receptacle extending into the implantable active medical device, and a solid state light source disposed within the hermetic cavity and optically coupled to the lead connector receptacle.

In another illustrative embodiment, an implantable active medical device system includes an implantable active medical device and a lead extending between a proximal end and a distal end. The implantable active medical device includes a housing defining a hermetic cavity, a lead connector receptacle extending into the implantable active medical device, and a solid state light source disposed within the hermetic cavity and optically coupled to the lead connector receptacle. A lead connector portion is disposed at the proximal end of the lead and is configured to mate with the lead connector receptacle.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "top", "bottom", "front", "rear", "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if an element depicted in the figures is turned over or flipped over, portions previously described as below or beneath other elements would then be above those other elements.

As used herein, when an element, component or layer is described as being "on", "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with" or "directly in contact with" another element, there are no intervening elements, components or layers for example.

The present disclosure relates to an implantable medical device with an optical lead connector. In particular the present disclosure relates to an implantable medical device having a lead connector receptacle that optically couples to a lead. An optical feedthrough forms a portion of the lead connector receptacle and a solid state light source is disposed within the implantable medical device hermetic housing. In many embodiments the lead connector receptacle extends into the hermetic cavity of the implantable medical device. An optical feedthrough preferably forms a closed end portion of the lead connector receptacle. A lead connector portion of a lead can mate with the lead connector receptacle and both optically couple and electrically couple to the lead connector receptacle to provide both light and electrical sensing and/or therapy to a distal end of the lead. While the present disclosure is not so limited, an appreciation of various aspects of the disclosure will be gained through a discussion of the examples provided below.

The implantable medical device and system described herein can perform optical stimulation techniques, such as optogenetic stimulation techniques and optionally electrical sensing and/or stimulation sequentially or simultaneously. The techniques may be capable of exciting or inhibiting neural activity in target neuron populations. For optogenetic stimulation, the target neurons may be selectively transfected with genes that express opsins that are activated by light emitted into the target tissue. The light may be selected to activate an opsin to initiate neuronal spikes or to deactivate or inhibit an opsin to cease or prevent neuronal spikes. The light may also be selected to activate an opsin to suppress a neuronal spike. An optogenetic stimulation system may be configured as an implantable medical device that can deliver optical stimulation through implantable optical fibers or other light-delivery apparatus to a target tissue, such as to specific or highly specific neuron populations. The high degree of specificity provided by the optical stimulation may limit or prevent stimulation of non-target tissue, possibly reducing side effects of stimulation.

Optical stimulation of the target tissue may be configured to cause optogenetic modulation of a selected target population of cells, such as, for example, a particular area of neurons within the brain or spinal cord or nervous system or cardiac system in general. The optogenetic modulation may activate light-sensitive channel proteins, referred to herein as "opsins," that are expressed within the target population of cells. Opsin expression may be triggered by a biological vector that introduces the opsin to the target neurons. In one example, the biological vector comprises a gene therapy agent, such as a lentivirus or retrovirus that is designed to selectively transfect a particular population of neurons to selectively deliver the genes to the target neurons that will express for the desired opsins. Optogenetic modulation may be particularly useful because the genetic modification provided by biological vectors allows a specific cell population to be targeted and transfected, without modifying neighboring cell populations so that when the area is exposed to stimulation light, only the selected and transfected cell population is actually stimulated. Thus, biological vectors, such as lentiviral-based or retroviral-based vectors, provide for delivery of their genes, allowing for direct cellular targeting through genetic mechanisms as opposed to reliance on electrode positioning. This allows the "placement" of the therapeutic stimulation to be performed by a highly selective biological vector rather than relying on a surgeon who, no matter how skilled, cannot place an electrode with the same precision.

As non-limiting examples, the optical stimulation may be delivered to target tissue within the brain or spinal cord of a human patient. However, the disclosure is not so limited. Rather, optical stimulation with optional electrical sensing and/or stimulation may be delivered to any of a variety of target tissue sites to support any of a variety or therapies. A few examples include, without limitation, cardiac tissue to support cardiac therapy such as pacing, cardioversion, defibrillation, resynchronization, or other therapies, gastrointestinal tissue to support gastrointestinal therapy such as therapy to address obesity, motility disorders (e.g., gastroparesis), dyspepsia, or other therapies, pelvic floor tissue (e.g., sacral or pudendal nerve tissue) to support pelvic floor therapy such as pain therapy, urinary or fecal incontinence therapy, sexual dysfunction, or other therapies, or cranial tissue to support cranial nerve therapy such as therapy to relieve occipital neuralgia, trigeminal neuralgia, facial pain, migraine headaches, or the like.

The optogenetic system may be fully implantable in the patient. In other examples, some portions of the optogenetic stimulation system may be implantable in the patient, while other components are configured to be external to the patient. For example, one or more programmers may be external to the patient, and communicate with an implanted stimulation device via wireless telemetry. In other cases, a stimulation generator may be external to the body, and be configured to deliver electricity, light, receive sensed signals, and/or deliver fluid via percutaneously implanted optical delivery elements (such as optical fibers), leads and/or conduits. Optical fibers are described for purposes of illustration, but without limitation. In some cases, optical fibers, and electrical leads may be constructed as separate elements, or two or more of such components combined with one another in a lead or other elongated element.

The terms "light" or "optical light" as used herein refer to electromagnetic radiation having a wavelength and intensity that has a physiologically measurable effect and may include visible light, infrared light, and ultraviolet light. In some examples, light that may be used to provide the optical stimulation of system may include visible light having a wavelength of between about 380 nm and about 750 nm, infrared light having a wavelength of between about 700 nm and about 300 μm, and ultraviolet light having a wavelength between about 10 nm and about 400 nm. For example, a first optical fiber may deliver visible light having a certain wavelength and intensity, and a second optical fiber may deliver visible light having the same wavelength and intensity, or a different wavelength at the same intensity, or the same wavelength and a different intensity, or the second optical fiber may deliver non-visible light, such as infrared or ultraviolet light. The one or more optical fibers and may be coupled to the same light source or different light sources. In some cases, a single light source may be optically multiplexed across the plurality of fibers to deliver light via the different fibers at different times or to different light emissive elements on the lead.

The optical fibers in the lead or in the medical device may be deployed to a target site as part of one or more bundles of optical fibers, such as an implantable optical fiber bundle, or separately. In some cases, stereotactic or other positioning techniques may be used to precisely position the optical fibers with respect to target tissue sites. The optical stimulation may be in the form of optical light of a particular wavelength and may be delivered as pulses, e.g., with a defined pulse width and pulse rate, or a sine-wave or other light emission transmission pattern or form. Various parameters of the pulses may be defined by a stimulation program. The optical and/or electrical pulses may be independently delivered substantially continuously for a relatively long period of time, such as several seconds or more, or in pulse bursts, segments, or patterns, and may be delivered alone or in combination with pulses defined by one or more other stimulation programs.

Figure 1:
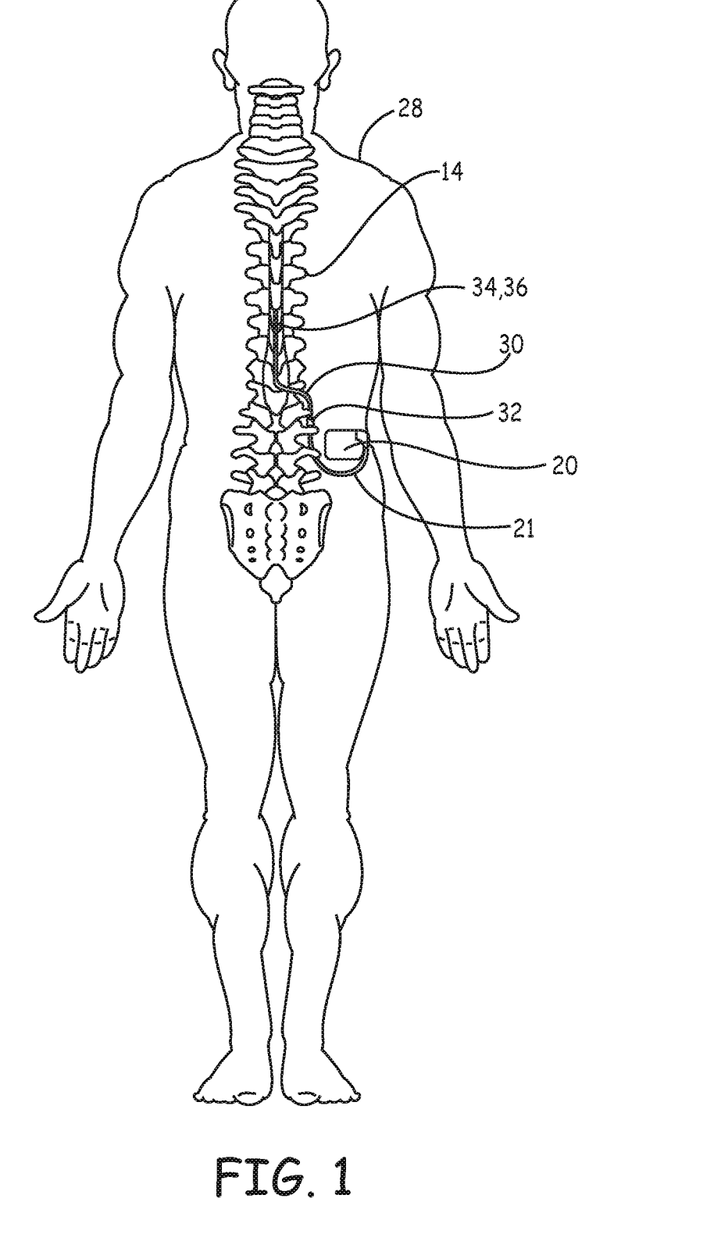
FIG. 1 is a schematic diagram of an active medical device implanted within a human body.
Figure 2:
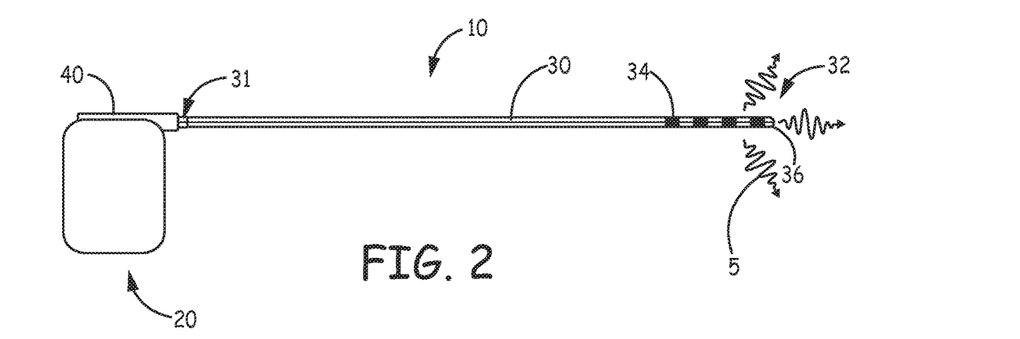
FIG. 2 is a schematic diagram of an active medical device system.

FIG. 1 is a schematic diagram of an active medical device 20 implanted within a human body of patient 28. FIG. 2 is a schematic diagram of an active medical device system 10 showing light 5 being emitted from a distal end 32 of the lead 30. The implanted active medical device 20 is illustrated as a neurostimulator, however, the implanted active medical device 20 can be any "active implantable medical device" or "implantable signal generator" as described above and can be placed in any location within a body cavity or tissue within the body, or on the surface of a patient's skin, as desired. This device can provide both electrical and optical stimulation therapy.

The active medical device 20 can be coupled to a lead extension 21 having a proximal end 31 coupled to the active medical device 20, and a lead 30 having a proximal end 31 coupled to a distal end 32 of the lead extension 21 and a distal end 32 of the lead 30 coupled to one or more electrodes 34 and/or optical windows or light emissive segments 36 emitting light 5. In other embodiments, the lead 30 proximal end 31 defines a lead connector and is coupled to a lead connector receptacle 40 of the active medical device 20, without a need for a lead extension 21. The active medical device 20 can be implanted in any useful region of the body such as in the abdomen of a patient 28, and the lead 30 is shown placed somewhere along the spinal cord 14 or in the upper body for brain stimulation.

These implantable medical device systems can also include a physician programmer and a patient programmer (not shown). The active medical device 20 can be considered to be an implantable signal generator of the type available from Medtronic, Inc. and capable of generating one or more optical and/or electrical signals occurring either simultaneously or one signal shifting in time with respect to the other, and having independently varying amplitudes and signal widths. The active medical device 20 contains a power source and the electronics for sending precise, electrical and/or optical signals to the patient to provide the desired treatment therapy.

Figure 3:
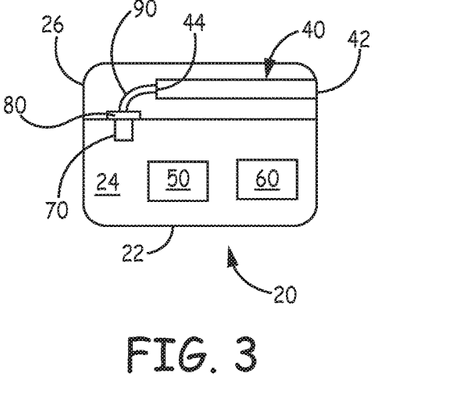
FIG. 3 is a schematic cross-sectional diagram of an illustrative active medical device.
Figure 4:
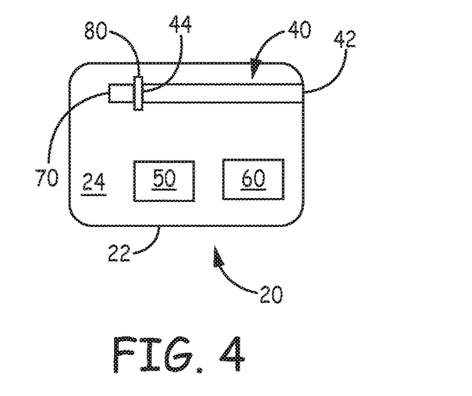
FIG. 4 is a schematic cross-sectional diagram of another illustrative active medical device.

FIG. 3 is a schematic cross-sectional diagram of an illustrative active medical device 20. FIG. 4 is a schematic cross-sectional diagram of another illustrative active medical device 20. The active medical device 20 includes a housing 22 defining a hermetic cavity 24. A lead connector receptacle 40 extends into the implantable active medical device 20. A solid state light source 70 is disposed within the hermetic cavity 24 and is optically coupled to the lead connector receptacle 40.

A hybrid or electronics 50 and a power source or battery 60 are located within the hermetic cavity 24. The electronics 60 generally control the active medical device. In some embodiments, the electronics 50 include memory. The memory can be any magnetic, electronic, or optical media, such as random access memory (RAM), read-only memory (ROM), electronically-erasable programmable ROM, flash memory, or the like. The power source 60 can have a number of different sizes or capacities or configurations as required by different optical and/or electrical therapy indications. The power source 60 can be electrically connected to the electronics 50 and solid state light source 70 via electrical interconects. The power source 60 can be any useful battery or inductive coil.

The solid state light source 70 can be any useful solids state light element. Solid state light elements include light emitting diodes (LEDs), organic light emitting diodes (OLEDs), laser diodes, vertical cavity surface emitting lasers (VCSELs) and polymer light emitting diodes, for example. The solid state light source 70 can be optically coupled to an optical feedthrough 80 to transmit light through the hermetic enclosure to the optical fiber 35 in the lead 30.

The optical feedthrough 80 can be any useful hermetic light transmissive element. In many embodiments the optical feedthrough 80 is formed of sapphire or glass material. The optical feedthrough 80 can be hermetically sealed to the lead connector receptacle 40 (see FIG. 4) or the hermetic cavity 24 (see FIG. 3). The optical feedthrough 80 can be hermetically sealed via brazing or diffusion bonding to the lead connector receptacle 40 (see FIG. 4) or the hermetic cavity 24 (see FIG. 3).

The lead connector receptacle 40 has a length that extends from a first open end 42 to a closed end 44. The lead connector receptacle 40 is configured to mate with a lead connector 31 of a lead 30. The lead connector receptacle 40 can include an electrical contact 150 (see FIG. 5) configured to mate with an electrical contact element on the lead connector 31 engaged in the lead connector receptacle 40. The lead connector receptacle 40 includes an optical feedthrough 80 (see FIG. 5) configured to mate with an optical fiber element 35 on the lead connector 31 engaged in the lead connector receptacle 40.

Referring to FIG. 3, the lead connector receptacle 40 extends into a header element 26 disposed on the hermetic cavity 24 and an optical feedthrough 80 between the header 26 and the hermetic cavity 24 optically couples the solid state light source 70 to the lead connector receptacle 40. A light guide or optical fiber 90 optically couples the optical feedthrough 80 to the lead connector receptacle 40. The solid state light source 70 can be directly fixed to the optical feedthrough 80, as illustrated. The header element 26 is not considered to be hermetic.

In many embodiments, the implantable active medical device 20 has a lead connector receptacle 40 extending into the hermetic cavity 24, as illustrated in FIG. 4. In these embodiments, the solid state light source 70 is optically coupled to an optical feedthrough 80 forming a portion of the lead connector receptacle 40. In many of these embodiments, the optical feedthrough 80 forms the closed end portion 44 of the lead connector receptacle 40. The solid state light source 70 can be directly fixed to the optical feedthrough 80, as illustrated. The lead connector receptacle 40 itself forms a portion of the hermetic enclosure 24. The lead connector receptacle 40 can extend between a first open end 42 and the optical feedthrough 80 closed end 44 and an electrical contact 150 (see FIG. 5) is configured to mate with an electrical contact element on a lead connector 31 engaged in the lead connector receptacle 40, and the electrical contact 150 (see FIG. 5) forms a portion of the lead connector receptacle 40 between the first open end 42 and the optical feedthrough 80 closed end 44.

Figure 5:
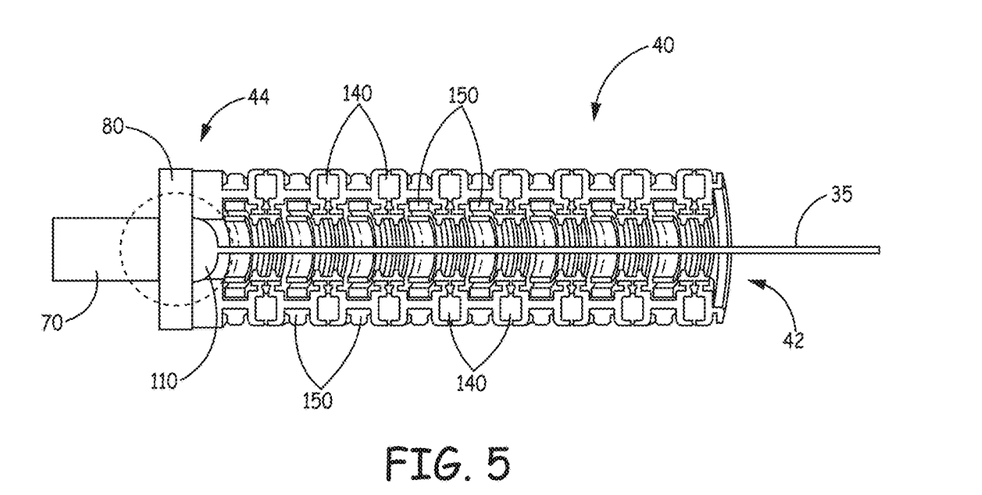
FIG. 5 is a schematic cross-sectional diagram of an illustrative lead connector receptacle.

FIG. 5 is a schematic cross-sectional diagram of an illustrative lead connector receptacle 40. The lead connector receptacle 40 extends between a first open end 42 and an optical feedthrough 80 closed end 44. A plurality of contact rings 150 are separated by insulating rings 140 and aligned in axial alignment and forming an annular receptacle having an inner surface defining an open lumen lead aperture. The optical feedthrough 80 forms the closed end portion 44 of the lead connector receptacle 40 and is hermetically bonded to or fixed to the lead connector receptacle 40, via brazing or diffusion bonding for example. The solid state light source 70 can be directly fixed to the optical feedthrough 80, as illustrated. The lead connector receptacle 40 itself forms a portion of the hermetic enclosure 24. The electrical contact rings 150 are configured to mate with electrical contact elements on a lead connector 31 engaged in the lead connector receptacle 40, and the electrical contact rings 150 form a portion of the lead connector receptacle 40 between the first open end 42 and the optical feedthrough 80 closed end 44. In many embodiments, the plurality of alternating contact rings 150 and insulating rings 140 are joined together by laser welding or brazing to form a hermetic tube. The optical feedthrough 80 can be hermetically fixed to the end of the lead connector receptacle 40 to form the closed end portion 44 of the lead connector receptacle 40. In some embodiments the optical feedthrough 80 can be hermetically fixed to an insulating ring 140 of the lead connector receptacle 40. In other embodiments the optical feedthrough 80 can be hermetically fixed to an electrical conducting contact ring 150 of the lead connector receptacle 40.

An optical coupling element 110 can contact the optical feedthrough 80 and be disposed within the lead connector receptacle 40. The optical coupling element 110 can be any light transmissive material having an index of refraction substantially equal to the index of refraction of both the optical fiber 35 and the optical feedthrough 80. The optical coupling element 110 assists in optically coupling the optical feedthrough 80 to the optical fiber 35 of the lead 30.

The electrically conducting contact rings 150 can be formed of any useful electrically conductive material and also form a hermetic barrier. In many embodiments, the electrically conducting contact rings are formed of a metallic material such as, for example, titanium, stainless steel, MP35N, niobium, tantalum, platinum, and alloys or combinations thereof. In some embodiments, the electrically conducting contact rings are formed of a metallic material such as, for example, titanium.

The electrically insulating material or rings 140 can be formed of any useful electrically insulating material. In many embodiments the electrically insulating material 140 is a ceramic or glass material. Glass for formation of the electrical insulating member 140 includes boro-alumino, boro-alumino silicate and/or boro-silicate type glasses. The element(s) and/or compounds used to form the electrical insulating member 140 are selected in a manner to reduce tensile stresses with conducting contact rings 150. For example, the electrical insulating member 140, employing glass, has a coefficient of thermal expansion (CTE) value about equivalent to or within 15% of the CTE associated with conducting contact rings 150.

In some embodiments, a filtering capacitor is disposed between the electrically conducting contact rings 150 and the electronics 50. The filtering capacitor can effectively filter out undesirable electromagnetic interference (EMI) from the active medical device 20.

Figure 6:
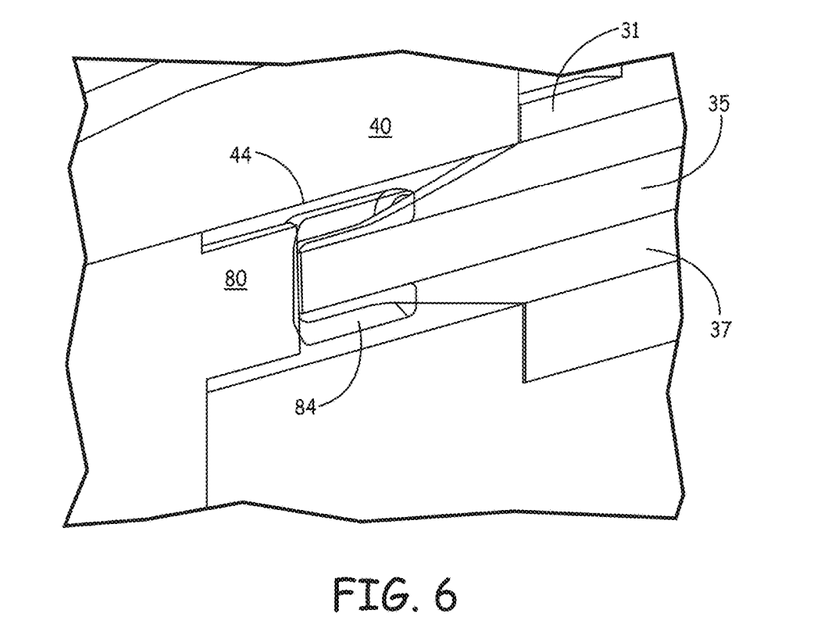
FIG. 6 is a schematic cross-sectional diagram of an illustrative lead connector receptacle being optically coupled to an illustrative lead.
Figure 7:
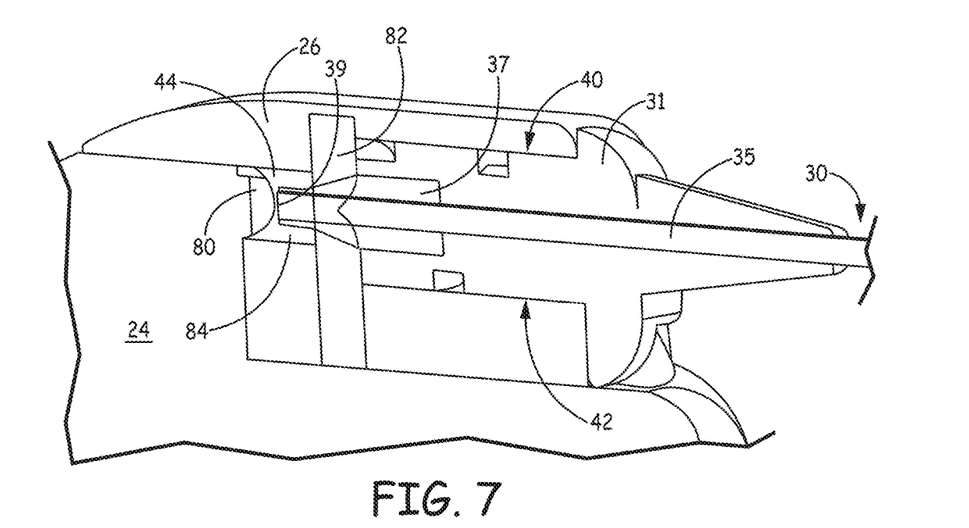
FIG. 7 is a schematic cross-sectional diagram of an illustrative lead connector receptacle being optically coupled to an illustrative lead.
Figure 8A:
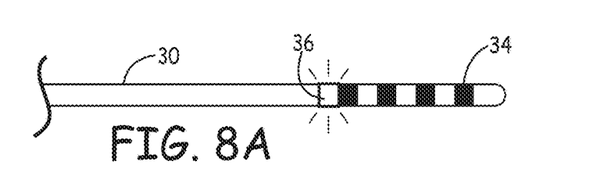
FIG. 8A-8E are side elevation views of illustrative lead distal ends illuminating light emission segments.
Figure 8B:
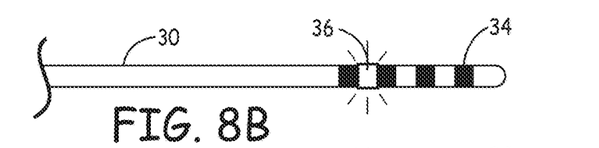
Figure 8C:
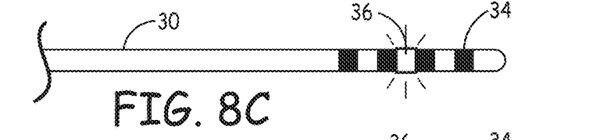
Figure 8D:
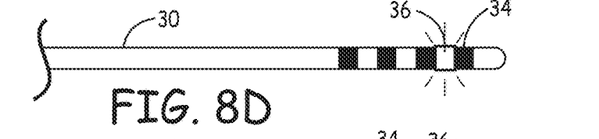
Figure 8E:
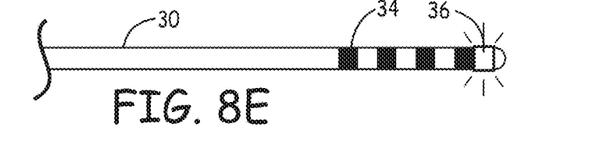

FIG. 6 is a schematic cross-sectional diagram of an illustrative lead connector receptacle 40 optically coupled to an illustrative lead connector 31. FIG. 7 is a schematic cross-sectional diagram of an illustrative lead connector receptacle 40 being optically coupled to an illustrative lead connector 31. While FIG. 6 and FIG. 7 illustrate only an optical connection, it is understood that the additional electrical contact elements of FIG. 5 can be utilized in FIG. 6 and FIG. 7.

Referring to FIG. 6, the optical fiber 35 of the lead 30 can be disposed within a cladding material 37 at the tip portion of the lead connector 31. The tip portion can press against an optical coupling element 84 located at the closed end portion 44 of the lead connector receptacle 40. The optical coupling element 84 can be any light transmissive material having an index of refraction substantially equal to the index of refraction of both the optical fiber 35 and the optical feedthrough 80. The optical coupling element 84 assists in optically coupling the optical feedthrough 80 to the optical fiber 35 of the lead 30. In some embodiments the optical coupling is achieved via evanescent coupling.

Referring to FIG. 7, the optical fiber 35 of the lead 30 can be disposed within a cladding material 37 at the tip portion 39 of the lead connector 31. The tip portion 39 can pierce a septum 82 enclosing an index matching fluid reservoir 84 located at the closed end portion 44 of the lead connector receptacle 40. The index matching fluid reservoir 84 can be any light transmissive fluid having an index of refraction substantially equal to the index of refraction of both the optical fiber 35 and the optical feedthrough 80. The index matching fluid reservoir 84 assists in optically coupling the optical feedthrough 80 to the optical fiber 35 of the lead 30. The septum 82 can be formed of any resilient material that can be pierced by the tip portion 39 of the lead connector 31. The lead connector 31 is illustrated engaged with the lead connector receptacle 40 disposed in a header 26, but is it understood that the lead connector receptacle 40 can be configured to extend into the hermetic cavity 24 as illustrated in FIG. 4.

FIGS. 8A-8E are side elevation views of illustrative lead 30 distal ends illuminating light emission segments 36. These figures illustrate the selective illumination or light emission from one of the five individual light emission segments 36. The light emission segments 36 are separated by electrode 34 segments. There are five individual light emission segments 36 separated by four electrode 34 segments. Light can be selectively emitted from one or more of the individual light emission segments 36. Electricity can be selectively provided to one or more of the individual electrode 34 segments. In many embodiments, the one or more optical fibers 35 can run the length of the lead 30 and the one or more conductors can be wound in a coil about the one or more optical fibers 35.

The individual light emission segments 36 can be independently illuminated in a number of ways. In some embodiments the individual light emission segments 36 are optically coupled to separate optical fibers that can be individually illuminated. In other embodiments the individual light emission segments 36 are individually illuminated by moving an single optical fiber along a length of the lead 30 distal end and illuminating the light emission segment proximate to the light emitting end or portion of the optical fiber. The individual light emission segments 36 can be formed of any useful light transmissive material such as a glass or sapphire ring of material.

Thus, embodiments of the IMPLANTABLE DEVICE WITH OPTICAL LEAD CONNECTOR are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. An implantable active medical device comprising a hermetic cavity defined by a hermetic enclosure, the medical device comprising:
    a housing defining a housing cavity and forming a first portion of the hermetic enclosure defining the hermetic cavity;
    a lead connector receptacle configured to mate with a lead and defining a length extending into the housing cavity, the lead connector receptacle comprising contact rings separated by insulating rings in axial alignment defining a hermetic tube forming a second portion of the hermetic enclosure even when a lead is not mated to the lead connector receptacle;
    an optical feedthrough disposed in the housing cavity and hermetically bonded to the lead connector receptacle to form a closed end portion of the hermetic tube and forming a third portion of the hermetic enclosure, the optical feedthrough configured to transmit light through the hermetic enclosure; and
    a solid state light source disposed within the hermetic cavity and optically coupled to the optical feedthrough of the lead connector receptacle.

2. The implantable active medical device according to claim 1 wherein the lead connector receptacle comprises an electrical contact configured to mate with an electrical contact element on a lead connector engaged in the lead connector receptacle.

3. The implantable active medical device according to claim 1 wherein the optical feedthrough defines a closed end surface of the lead connector receptacle.

4. The implantable active medical device according to claim 3 wherein the lead connector receptacle extends between an open end and the optical feedthrough closed end and wherein an electrical contact, configured to mate with an electrical contact element on a lead connector engaged in the lead connector receptacle, forms a portion of the lead connector receptacle between the open end and the optical feedthrough closed end.

5. The implantable active medical device according to claim 1 wherein a light guide optically couples the optical feedthrough to the lead connector receptacle.

6. The implantable active medical device according to claim 1 wherein the lead connector receptacle comprises an optical coupling element contacting the optical feedthrough and within the lead connector receptacle, the optical coupling element having a matching index of refraction with the optical feedthrough.

7. An implantable active medical device system comprising a hermetic cavity defined by a hermetic enclosure, the medical device system comprising:
    an implantable active medical device comprising:
        a housing defining a housing cavity and forming a first portion of the hermetic enclosure defining the hermetic cavity;
        a lead connector receptacle configured to mate with a lead and defining a length extending into the housing cavity, the lead connector receptacle comprising contact rings separated by insulating rings in axial alignment defining a hermetic tube forming a second portion of the hermetic enclosure even when a lead is not mated to the lead connector receptacle;
        an optical feedthrough disposed in the housing cavity and hermetically bonded to the lead connector receptacle to form a closed end portion of the hermetic tube and forming a third portion of the hermetic enclosure, the optical feedthrough configured to transmit light through the hermetic enclosure;
        a solid state light source disposed within the hermetic cavity and optically coupled to the optical feedthrough of the lead connector receptacle; and
    a lead extending between a proximal end and a distal end, a lead connector portion disposed at the proximal end and configured to mate with the lead connector receptacle.

8. The implantable active medical device system according to claim 7, wherein the lead comprises an optical fiber and an electrical conductor extending along a length of the lead.

9. The implantable active medical device system according to claim 7, wherein the lead extends between a proximal end portion and a distal end portion and a lead connector is disposed at the proximal end portion and the lead connector is both electrically and optically coupled to the lead connector receptacle.

10. The implantable active medical device system according to claim 9, wherein the distal end portion comprises an electrode that is electrically coupled to the lead connector receptacle and an optical window that is optically coupled to the lead connector receptacle.

11. The implantable active medical device system according to claim 10, wherein the distal end portion comprises a plurality of optical windows spaced apart along a length of the distal end portion of the lead.

12. The implantable active medical device system according to claim 7 further comprising an optical coupling element within the lead connector receptacle and contacting both the lead connector receptacle and the lead, the optical coupling element having a matching index of refraction with the optical feedthrough.

13. The implantable active medical device system according to claim 7 wherein the optical feedthrough defines a closed end surface of the lead connector receptacle.

14. The implantable active medical device system according to claim 13, wherein the lead connector receptacle extends between an open end and the optical feedthrough closed end and wherein an electrical contact, configured to mate with an electrical contact element on a lead connector engaged in the lead connector receptacle, forms a portion of the lead connector receptacle between the open end and the optical feedthrough closed end.

* * * * *